United States Patent [19]

Blattler et al.

[11] Patent Number: 4,764,368

[45] Date of Patent: Aug. 16, 1988

[54] ACID-CLEAVABLE COMPOUND

[75] Inventors: Walter A. Blattler; John M. Lambert, both of Brookline, Mass.

[73] Assignee: Dana-Farber Cancer Institute, Inc., Boston, Mass.

[21] Appl. No.: 908,388

[22] Filed: Sep. 17, 1986

Related U.S. Application Data

[60] Continuation-in-part of Ser. No. 733,479, May 13, 1985, Pat. No. 4,618,492, which is a division of Ser. No. 645,614, Aug. 29, 1984, Pat. No. 4,542,225.

[51] Int. Cl.$^4$ .................. C07D 519/00; C07D 521/00
[52] U.S. Cl. ........................................ 424/85; 424/86; 424/87; 424/88; 435/174; 435/177; 435/181; 514/2; 514/3; 530/300; 530/350
[58] Field of Search ................... 424/85, 86, 87, 88; 435/174, 177, 181; 514/2, 3, 579; 530/300, 350

[56] References Cited

U.S. PATENT DOCUMENTS

| | | | |
|---|---|---|---|
| 2,197,574 | 4/1938 | Watt | 548/517 |
| 3,455,832 | 7/1969 | Davis | 548/517 |
| 4,107,174 | 8/1978 | Baumann et al. | 548/517 |
| 4,150,033 | 4/1979 | Kitagawa | 548/544 |
| 4,359,457 | 11/1982 | Neville et al. | 424/85 |
| 4,410,542 | 10/1983 | Iwao et al. | 548/517 |
| 4,618,492 | 10/1986 | Blattler et al. | 424/85 |

OTHER PUBLICATIONS

Carlsson et al., *Biochem. J.* (1978), vol. 173, pp. 723–737, "Protein Thiolation and Reversible Protein-Protein Conjugation".
Cleland, W. W. (1964), Bioch. 3:480.
Lutter et al., (1974), FEBS Letters, 48:288–292.
Shen and Ryser (1981), Biochem. and Biophys. Res. Commun., 102(3):1048–1054.
Vitetta et al. (1983), Science 219:644–650.
Edwards (1983), Pharmacol. Ther. 23:147–177.
Ramakrizhnan et al. (1984), Cancer Research 44:1398–1404.
Ritz et al. (1980), Nature, 283:583–585.
Barbieri et al. (1982), Biochem. J., 203:55–59.
Stirpe et al. (1980), J. Biol. Chem., 255:6947–6953.
Kirby et al. (1970), Proc. Biochem. Soc. Symp., 31:99–103.
Dixon et al. (1968), Biochem. J., 109:312–314.

Primary Examiner—Delbert R. Phillips
Assistant Examiner—Nathan M. Nutter

[57] ABSTRACT

Heterobifunctional reagents that are cleavable under mildly acidic conditions are disclosed. The reagents include an acid cleavable cyclohexene-1,2,-dicarboxylic acid monoamide group. Also disclosed are methods of making the cross-linkers, as well as methods of using the cross-linkers, e.g., to deliver a biologically active substance across the membranes of selected cells in a heterogeneous cell population; once inside the cell the active substance is released, intact, by the transient, mild acidity of certain cell structures. Finally, a method of characterizing complex multi-chain protein structures is disclosed.

20 Claims, 5 Drawing Sheets

ACID-CLEAVABLE COMPOUND

This invention was made with Government support. The Government has certain rights in this invention.

This application is a continuation-in-part of co-pending, commonly owned U.S. patent application Ser. No. 733,479 now U.S. Pat. No. 4,618,492, filed on May 13, 1985 and which is a Divisional application of commonly owned U.S. patent application Ser. No. 645,614, now U.S. Pat. No. 4,542,225, filed Aug. 29, 1984 by Walter A. Blattler, John M. Lambert, and Peter D. Senter, which applications are hereby incorporated by reference.

BACKGROUND OF THE INVENTION

This invention relates to controlled release to a liquid medium of substances having an amino group; the invention also relates to compounds used in such release, and to precursors in the synthesis of such compounds.

There are numerous situations in which it is desirable to control the release of amino-group-containing substances to a liquid medium. By way of example, it may be desirable to control the release of an amino-group-containing drug or cytotoxin to a cell population or specific members of a cell population. It may also be desirable to control cleavage of various cross-linked proteins or peptides, for example, in analyzing the spatial relationships in a complex of large amino-group-containing molecules such as peptides or proteins. [The term "peptide" will be used in this application to include proteins, no matter how large, as well as shorter-chain peptides.]

One specific situation in which controlled release is desirable is delivering a biologically active compound through the cell membrane to inner cell structures, for example where the compound has a diminished effect if trapped in the medium outside the cell membrane but is more potent once released inside the cell.

It is also desirable to deliver biologically active compounds to selected cells in a heterogeneous cell population. For example, in treating diseased or infected cells such as virus-infected cells or transformed or malignant cells, it is desirable to deliver cytotoxins to the diseased or malignant cells but not to normal cells.

One approach disclosed for targeting biologically active compounds to malignant cells uses an antibody-toxin conjugate. The antibody is specific for malignant cells and delivers the toxin to them. To be effective, such systems should deliver the toxin with high selectivity to the target cells without unnecessarily reducing the effectiveness of the active substance. These problems are particularly important where the goal is destruction of infected or diseased cells in vivo without harming normal cells.

Some of these approaches require that the antibody-toxin conjugate retain the toxicity of the toxin component. Other approaches depend on disulfide bond cleavage, a phenomenon that may be difficult to control temporally and spatially to avoid release of the toxin before delivery to the targeted cells.

SUMMARY OF THE INVENTION

The invention features heterobifunctional compounds that are stable under mildly basic conditions (e.g. $\geq$ pH 7.2), but are cleaved remarkably rapidly under mildly acid conditions (e.g. $\leq$ pH 6.4). The invention also features precursors to the heterobifunctional compounds.

The heterobiofunctional compounds have the formula:

where X is an amino-group containing substance whose amino nitrogen forms an amide link with the carbonyl group of the cyclohexene-1, 2, dicarboxylic acid function; $R_1$, $R_2$, and $R_3$ are independently selected from hydrogen, alkyl, or phenyl groups; and F comprises an organic macromolecule function from which the amino-group containing substance is to be released.

Preferably, X comprises a polypeptide drug or enzyme. For example, X can be a cytotoxin residue, such as a cytotoxin that inactivates cellular protein synthesis. Also preferably, F is A—CO—NH—, or A—CO—O—, where A comprises the organic macromolecule; for example A can be a polymeric carrier, an N-alkyl maleimido-linked polypeptide, or a thioether-linked polypeptide. Most preferably, $R_1$, $R_2$, and $R_3$ are -H, and F can be bonded to the cyclohexene ring either alpha or beta to the C=C. In one preferred embodiment, the organic macromolecule is an antibody or other binding partner that is specific for a cell-surface receptor.

The compound is generally useful for releasing biologically active amino-containing compounds, such as peptides or proteins and drugs, from carriers, including solid phase carriers, under relatively mild conditions with the specific ability to control release. The compound specifically is useful for selectively killing cells in a heterogenous cell population, for example, when removing one type of cell from a heterogenous cell culture or from a higher organism.

One advantage of the compound lies in its stability under basic (e.g. pH $\geq$ 7.2) conditions and its rapid cleavage under relatively mild acid conditions, e.g., pH $\leq$ 6.5 which is advantageous, for example, when the compound is used to release a drug within living cells. Specifically, intracellular organelles (such as endosomes or lysosomes) exhibit an acidic microenvironment of about pH 4.5 to 5.5. Thus, the compound can be used for rapid release at the desired intracellular location. By targeting the cytotoxin so precisely, less toxin is needed for a given cell population, and there is less chance for contamination of non-targeted cells.

In particular, the compound can include a cell receptor binding partner which selectively binds to cells of a desired cell type; when the reagent is internalized by those cells by cytosis, it encounters acidified organelles where it is cleaved. Accordingly, the invention also features methods of using the heterobifunctional compound as outlined above.

The invention also features novel precursors used to synthesize the heterobifunctional reagent, having the formula:

where:
(a) $R_1$, $R_2$, $R_3$ are independently selected from hydrogen, alkyl, or phenyl groups;
(b) T is selected from —OH, —NH$_2$, where Z is an N-alkyl maleimido group, I—CH$_2$— or Br—CH$_2$—; and
(c) U and V are independently selected from —OH, and OR$_4$ (R$_4$ being a phenyl group or an alkyl group of C$_5$ or less).

Finally, methods of making heterobifunctional compounds are featured in which one of the following compounds is provided and then reacted with a functionalized protein:

where: X is defined in claim 1, r=1–5, $R_1$, $R_2$, and $R_3$ are as defined above, and $R_5$ is —CH$_2$I or —CH$_2$—Br.

The precursors are useful for synthesizing the bifunctional cell-delivery compounds. Alternatively, the precursors can be used to cross-link components of a biological system with a linkage that is easily cleaved by acid. Using the designations in the above formulas, the bifunctional compound formed would cross-link X with the organic macromolecule of F.

Other features and advantages of the invention will be apparent from the following description of the preferred embodiment and from the claims.

DESCRIPTION OF THE PREFERRED EMBODIMENTS

We turn now to a description of the preferred embodiments of the invention, first briefly describing the drawings thereof.

BRIEF DESCRIPTION OF THE DRAWINGS

FIGS. 1–5 show the steps in the synthesis of five different heterobifunctional acid-cleavable compounds.

FIG. 2 shows the steps in the synthesis of Compound B.

FIG. 3 shows the steps in the synthesis of Compound C.

FIG. 4 shows the steps in the synthesis of Compound D.

FIG. 5 shows the steps in the synthesis of Compound E.

GENERAL

There are two particularly preferred embodiments of the invention. One is a cell-delivery agent for delivering a biologically active protein or peptide to a cell as described above. The other is a tool for evaluating a complex that includes one or more large amino-group-containing molecules, such as a ribosome complex or a multi-unit enzyme. By cross-linking members of the complex, it is possible to separate out the cross-linked components, and then to decouple the cross-linked components without altering their structure in order to analyze them. Analysis of the appearance and disappearance of members of the complex and of the cross-linked substance provides a tool for evaluating components of living systems and thereby to follow the effects of treatments of, and abnormalities in, these systems.

A. Cell-Delivery Embodiment

The preferred biologically active substance to be delivered to a cell is a protein, peptide drug, or an enzyme. In a particularly preferred embodiment, the active substance is a cell toxin to be delivered to selected cells. Such toxins include the pokeweed antiviral proteins PAP, PAPII, and PAP-S, described above and in Irvin (1975) Pharmac. Ther. 21:371–387. Other peptide cytotoxins include ricin A-chain, abrin A-chain, modeccin A-chain as well as gelonin and other single-chain ribosomal inactivating proteins such as those described in Barbieri et al. (1982) Cancer Surv. 1:489–520.

Peptide toxins are preferred because they are readily bound to the reagent and because they are extremely potent toxins which inhibit cell protein synthesis when present inside the cell in extremely minute quantities. Other amino-group-containing cytotoxins which are not peptides are also within the scope of the invention however; examples of such cytotoxins or cytotoxic drugs are melphalan, bleomycin, adriamycin, and daunomycin.

The above-described active substances are delivered to selected cells by binding partners to cell-surface features. The preferred binding partners are antibodies to cell antigens. Particularly preferred are monoclonal antibodies to cell surface antigens specific to diseased, infected, transformed or malignant, but not to normal cells. Particularly, but not exclusively, they are antibodies that are taken up by the cells. It is not necessary that normal (i.e., non-target) cells lack the specific antigen entirely, as long as the antigen is not present in sufficient numbers on those cells to permit significant uptake of the active substance by the cells.

One such antibody is J5, available from Coulter Immunology, Hialeah Florida. Other examples are antibodies to melanoma surface antigens such as those described by Imai et al. (1983) Cancer Imm. 15:206 et seq. Other suitable antibodies available from Coulter Immunology include the antibodies to surface antigens found on T-cells and T-cell lymphomas such T3, T4, T11, and T12.

Other binding partners in this embodiment include non-antibody cell membrane transport agents such as transferrin and protein hormones such as insulin, and lymphokines such as interleukin 2.

B. Biological System Evaluation

The preferred systems to be evaluated by cross-linking include cell structures such as ribosomes and membranes, and complex proteins. One component of the system (the macromolecule contained in "F" in the general formula) is functionalized with a sulfhydryl group, and the above-described precursor is used to cross-link that component to an amino-group-containing substance (X in the formula) that is adjacent to the sulfhydryl group. For example, a functionalized enzyme substrate may be used to establish the binding domain of the enzyme by cross-linking during the progress of the enzyme-catalyzed reaction.

The Compounds

The compounds used in the above systems include an amino-group-containing substance designated "X" in the claims, and an organic macromolecule included in claim element "F"; preferably, F is selected from polymeric carriers and polypeptides linked by a maleimido, or an N-substituted maleimido function or by one of the above-described organohalogen groups.

The amino-group-containing substance is joined to the bifunctional reagent via an amide linkage, and it is released from the reagent without alteration of its structure and activity. The amide linkage should be formed under mild conditions that do not affect protein structure; at that same time, the linkage should be strong and stable under all but acidic conditions and yet be rapidly cleaved under mild conditions (pH≦6.5), that is weakly acidic conditions compatible with sensitive components of a biological system. Since the cleavage site is at the bond between the amino group of the amino-group-containing substance and the remainder of the compound, the substance is released intact, with no additional component and with no deletions.

The bridge between the above-described maleimido or organohalogen entities and cyclohexene dicarboxylic acid entity is important because, if that bridge is cleaved by natural processes (e.g., by enzymes in an in vivo system) at an undesired time or place, the selectivity of the binding partner is lost, and the toxin, or a compound with potential toxic activity, is present in the medium outside the cells without a means for selecting the target cells. Other constraints on the bridge are compatibility and inertness with respect to other components of the complex and ease of formation under conditions that do not harm those components.

The preferred bridges are described above in detail in the Summary of the Invention.

For purposes of illustration, we will now describe the synthesis and use of specific representative examples of the following preferred compounds A–F.

Compound A

Figure 1:
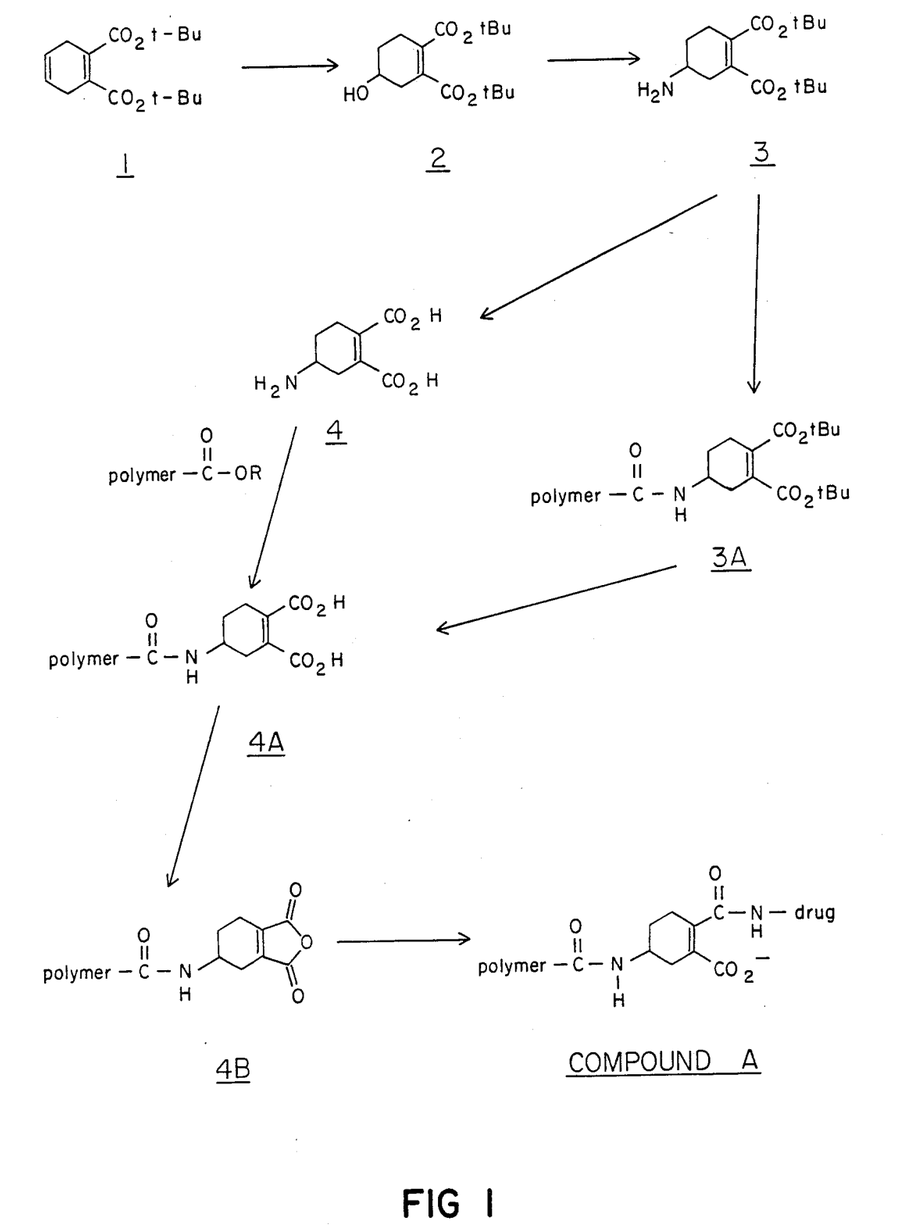
FIG. 1 shows the steps in the synthesis of Compound A, with an alternative synthesis from a polymeric substrate having multiple carboxylic acid groups.

In FIG. 1, compound A is synthesized as follows.

1,4-Cyclohexadienyl-1,2-dicarboxylic acid di-t-butylester (1) was prepared from butadiene and acetylene dicarboxylic acid di-t-butylester as described by Weber et al. (1980) Chem. Ber. 113:531, and was then subjected to a standard hydroboration reaction with diborane in tetrahydrofuran. Briefly, the diene 1 (9.82 g, 35 mmol) was dissolved in dry tetrahydrofuran (100 mL) and treated at 0° C. with an equimolar amount of borane-THF complex. After 0.5 h at 0° C., water (7 mL) was added, followed by 3 N NaOH (7 mL) and 30% hydrogen peroxide (7 mL). The solution was stirred at room temperature for 2 h and then concentrated under reduced pressure. The residue was extracted three times with ether and the combined ether solutions were washed with water, dried and concentrated to a viscous oil. The crude product was further purified by flash chromatography on silica gel with petroleum ether - ethyl acetate (7:3 v/v) as eluant, giving pure alcohol 4-Hydroxy-1-cyclohexenyl-1,2-dicarboxylic acid di-t-butylester 2.

The amine 4-Amino-1-cyclohexenyl-1,2-dicarboxylic acid di-t-butylester 3 could be prepared in 3 steps from the alcohol 2 in reasonable yield (about 55%) without purification of the intermediate products. Alcohol 2 (7.14 g, 23.9 mmol) and p-toluenesulfonylchloride (6.49 g, 33.5 mmol) were dissolved in dry pyridine (43 mL) and the solution was stirred at ambient temperature overnight. Water was then added (0.66 mL) and stirring was continued for another 0.5 h. The solution was then concentrated in the cold under reduced pressure, the residue taken up into ether and washed with cold 1 M sulfuric acid, 1 M sodium bicarbonate solution and water. After drying and removal of the ether, the crude tosylate was dried under high vacuum for 4 h and then dissolved in dry acetonitrile (90 mL). Sodium azide (1.94 g, 200 mmol) and 15-crown-5 (0.95 g, 4,3 mmol) were added and the solution was refluxed overnight under $N_2(g)$. The cooled solution was then filtered and concentrated to an oil which was redissolved in dry ether (100 mL) and subjected to a second filtration. Removal of the ether afforded a yellowish oil which was dissolved in dry methanol (75 mL) for the reduction of the azido group. 1,3-propanedithiol (6.49 g, 60 mmol) and triethylamine (6.07 g, 60 mmol, distilled from 1-naphthylisocyanate) were added and the mixture was stirred at room temperature under $N_2(g)$ for 40 h. The reaction mixture was then filtered and the filtrate concentrated on an aspirator with gentle heating, yielding an orange oil, which was purified by flash chromatography on silica gel. The column (200 mL) was first washed with $CHCl_3$ (500 ml) and $CHCl_3$-MeOH (95:5 v/v, 300 mL) and then eluted with $CHCl_3$-MeOH (80:20 v/v). Pure amine 3 was recovered as a colorless oil.

For the purpose of analysis, the azido intermediate 4-azido-1-cyclohexenyl-1,2-dicarboxylic acid di-t-butylester was purified from a small scale reaction by flash chromatography on silica gel (petroleum ether - ethyl acetate 95:5 v/v) and was obtained as a colorless oil.

Di-t-butylester 3 (0.122 g, 0.41 mmol) was dissolved in trifluoroacetic acid (1 mL) and the homogeneous solution was stirred at ambient temperature for 1 h. The solvent was then evaporated and the oily residue treated with dry ether, affording a white solid. $^1$H-NMR analysis showed that the esters had been completely cleaved but that the sample contained ether which was not removed with prolonged drying on the high vacuum. The sample was therefore dissolved in water (3 mL), the solution filtered and lyophilized, yielding 4-Amino-1-cyclohexenyl-1,2-dicarboxylic acid trifluoroacetic acid salt 4 as a white solid.

Compound 4 can be linked to a polymer carrier that has activated acid groups (such as the commonly used N-hydroxysuccinimide esters or p-nitrophenol esters), forming compound 4A. Compound 4A is a diacid which can be stored. When synthesis of compound A is desired, the diacid is converted to the corresponding anhydride (4B), as described below, which can then be used to link an amino-group-containing compound as described below, to yield compound A.

Specifically to convert the diacids such as compound 4A to anhydrides such as compound 4B, typically, a 1% solution (w/v) of diacid in dry DMSO is treated with 1.2 molar equivalents of dicyclohexylcarbodiimide at room temperature for 1 h. The solution is then filtered and the product precipitated with dry ether. When the reaction is performed on a microliter scale, filtration is replaced by centrifugation and the supernatant is either used directly for the modification of protein or was dropped into 10 volumes of dry ether. The quantitative nature of the reaction can be judged by thin-layer chromatography on silica gel (glass plates) in the solvent system toluene-dioxane-acetic acid (9:9:2).

FIG. 1 also shows an alternative synthesis of compound A from compound 3 and a polymeric substrate having multiple carboxylic acid groups.

For example poly-L-glutamic acid (PLG) available from Sigma Chemical Co., can be used as a starting resin. Specifically, PLG of an average length of 305 amino acids per polymeric molecule (1.39g, 10.8 mmol of monomeric unit) was dissolved in dry DMSO (10 mL) and treated first with 3 (482 mg, 1.62 mmol), 2-aminoethyl-2$^1$- pyridyldisulfide hydrochloride (48 mg, 0.2 mmol) [this functional group will be used later for linkage of compound A to an antibody], N, N$^1$- dicyclohexyl carbodiimide (458 µg, 2.2 mmol) and N-ethylmorpholine (1.63 mL, 12.8 mmol) at room temperature overnight. N-hydroxysuccinimide (1.13 g, 9.84 mmol) and additional carbodiimide (2.24 g, 10.7 mmol) and N-ethylmorpholine (1.16 mL, 9.2 mmol) were then added, followed after 8 h by a solution of concentrated aqueous ammonium hydroxide (3.6 mL of a 29% (w/w) solution). The final mixture was stirred overnight, then diluted with water to about 60 mL and treated with concentrated hydrochloric acid until the pH of the solution reached 7.2. The solution was then filtered through a Buchner funnel, concentrated to a small volume (5 to 10 ml) by evaporation and finally passed through a column (2.6×96 cm) of Sephadex G-25 (fine) equilibrated in 0.5 M triethylammonium bicarbonate buffer pH 7.2. The fractions containing the polymer eluted in the exclusion volume of the column and were combined. The combined solution was evaporated to dryness and the buffer salts were removed completely by three consecutive evaporations from water, yielding 3A as a white powder.

3A was then dissolved at ambient temperature in the minimal amount of trifluoroacetic acid and kept in solution for 1 h. Trifluoroacetic acid was then evaporated on an aspirator and the residue extentively washed with dry diethyl ether, yielding 4A in quantitative yield as a white powder.

Compound 4A (20 mg) was dissolved in dry dimethylsulfoxide (0.4 mL) and treated with N, N$^1$ dicyclohexyl carbodiimide (DCC, 8mg) for 1 hr at room temperature to produce compound 4B, which is recovered by precipitation with dry ether (5 mL) 4B was then redissolved in dimethylsulfoxide (0.4 mL) and adriamycin hydrochloride (17 mg) and triethylamine (0.005 mL) were added. After 1 hr, the polymeric drug carrier A was precipitated with diethyl ether (5 mL).

Compound B

Starting with compound 3, whose preparation is described above, compound B is synthesized as shown in FIG. 2.

Figure 2:
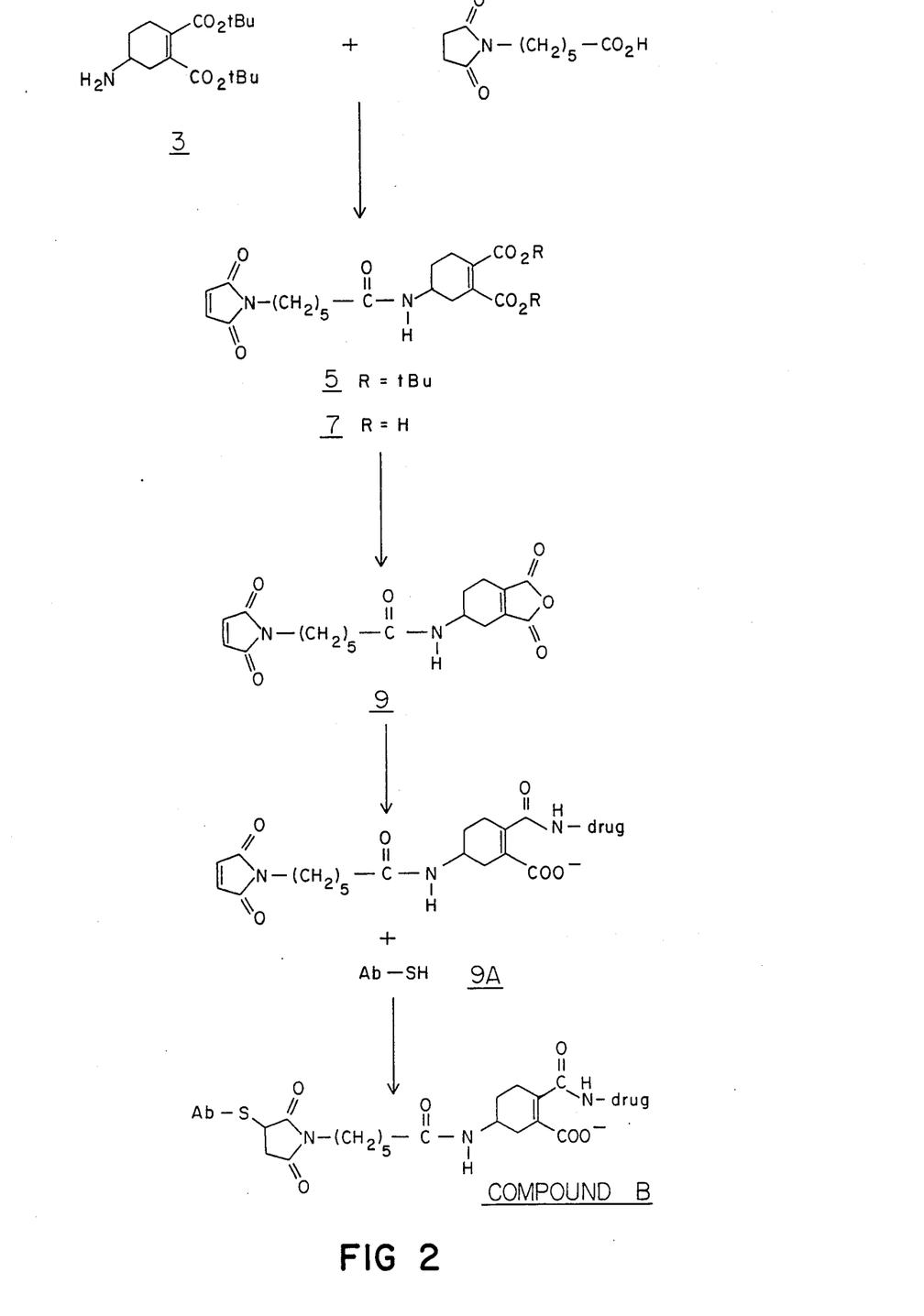

6-Maleimidocaproic acid was prepared according to the method of Keller and Rudinger cite (1974). A solution of 6-maleimidocaproic acid (1.53 g, 7.26 mmol) and N-ethylmorpholine (836 mg, 7.26 mmol) in dry THF (15 mL) at −15° C. was treated with iso-butylchloroformate (992 mg, 7.26 mmol) and stirred at −15° C. for 0.5 h. A solution of amine 3 (1.96 g, 6.6 mmol) in cold THF (10 mL) was then added and the reaction mixture was slowly warmed up to ambient temperature. After 2 h, the solution was filtered, the THF evaporated and the residue dissolved in ethyl acetate and washed with cold 0.1 M hydrochloric acid, 0.1 M sodium bicarbonate solution and water. After drying and concentration a viscous oil was obtained which was further purified by flash chromatography on silica gel with petroleum ether - ethyl acetate (50:50 v/v) affording pure diester N-(6-Maleimidocaproyl)-4-amino-1-cyclohexenyl-1,2-dicarboxylic acid di-t-butylester 5 as a viscous oil.

In general, diesters such as 5 and 6 can be converted into diacids 7 and 8 respectively using the technique described above for forming compound 4. The diacids can be stored, and freshly converted to anhydrides 9 and 10 respectively, as described above for converting 4A to 4B. Similarly, diacids 16 and 17 can be converted into anhydrides 18 and 19 by the same process.

Thus, Di-t-butylester 5 (1.27 g, 2.59 mmol) was treated with trifluoroacetic acid (12 mL) as described for the preparation of 4. The white solid obtained was ground-up finely and dried under high vacuum for 48 h; giving the compound N-(6-Maleimidocaproyl)-4-amino-1-cyclohexenyl-1,2-dicarboxylic acid 7.

Compound 7 is a stable diacid compound which is stored as such and converted to the corresponding anhydride compound 9 when the latter is used for the immediate preparation of compound B, as described below.

Compound C

Figure 3:
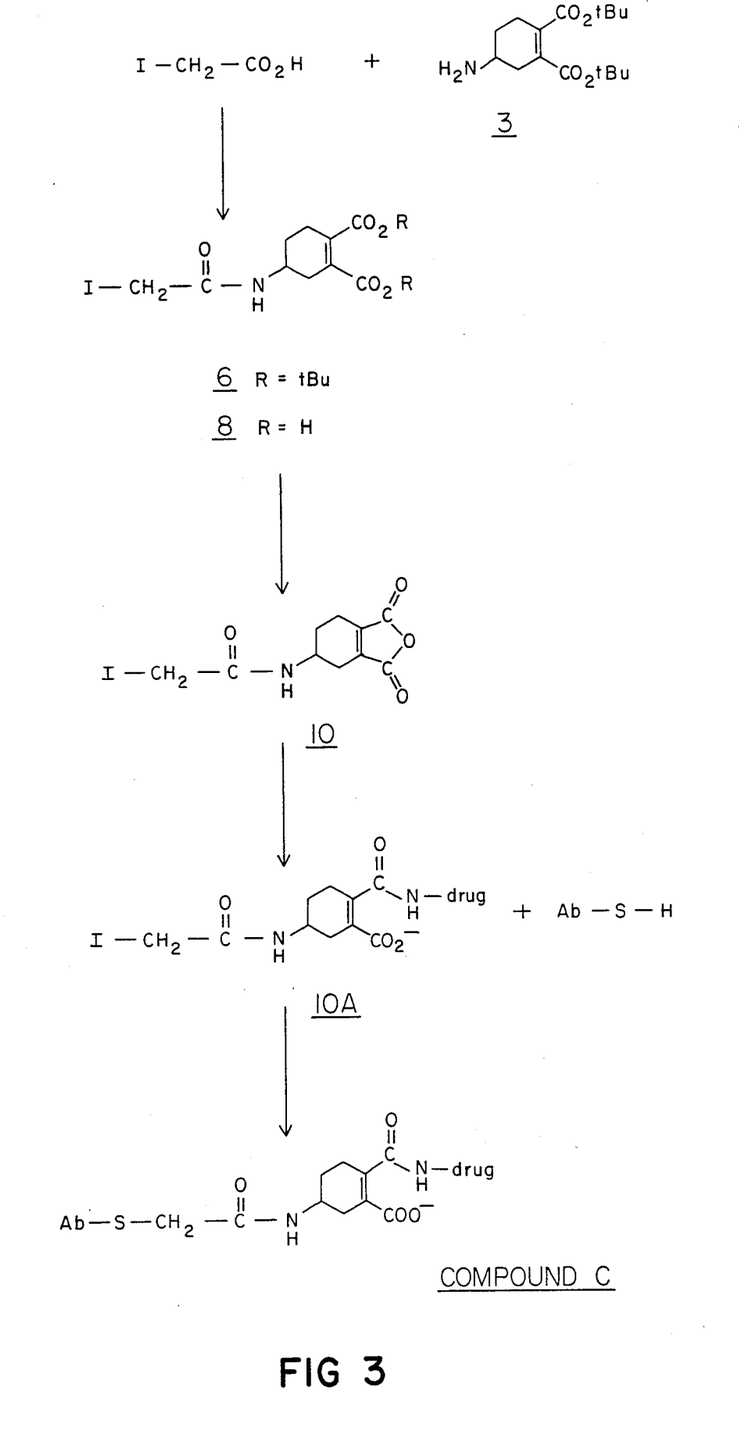

Amine 3 is prepared as described above for the synthesis of Compound A. Then the following steps are performed, as shown in FIG. 3.

Amine 3 (297 mg, 1 mmol), iodoacetic acid (186 mg, 1 mmol) and N-ethoxycarbonyl-2-ethoxy-1,2-dihydroquinoline (EEDQ, 250 mg, 1 mmol) were dissolved in dry dichloromethane (5 mL) and the solution was stirred under $N_2(g)$ at room temperature overnight. The reaction mixture was then poured onto cold 0.1 M hydrochloric acid and the product was extracted with ethyl acetate. The combined extracts were washed with water, dried and concentrated yielding pure 4-Iodoacetamido-1-cyclohexenyl-1,2-dicarboxylic acid di-t-butylester 6 as an oil, which solidified to a brittle foam upon drying under high vacuum.

By analogy to the preparation of 7, di-t-butylester 6 (0.412 mg, 0.88 mmol) was converted with trifluoroacetic acid (4 mL) quantitatively into the diacid 4-Iodoacetamido-1-cyclohexenyl-1,2-dicarboxylic acid 8.

Diacid 8 is stored and, as needed, is converted to the corresponding anhydride 10 which can be used to form compound 10A and Compound C, which is described in greater detail below.

Compound D

Figure 4:
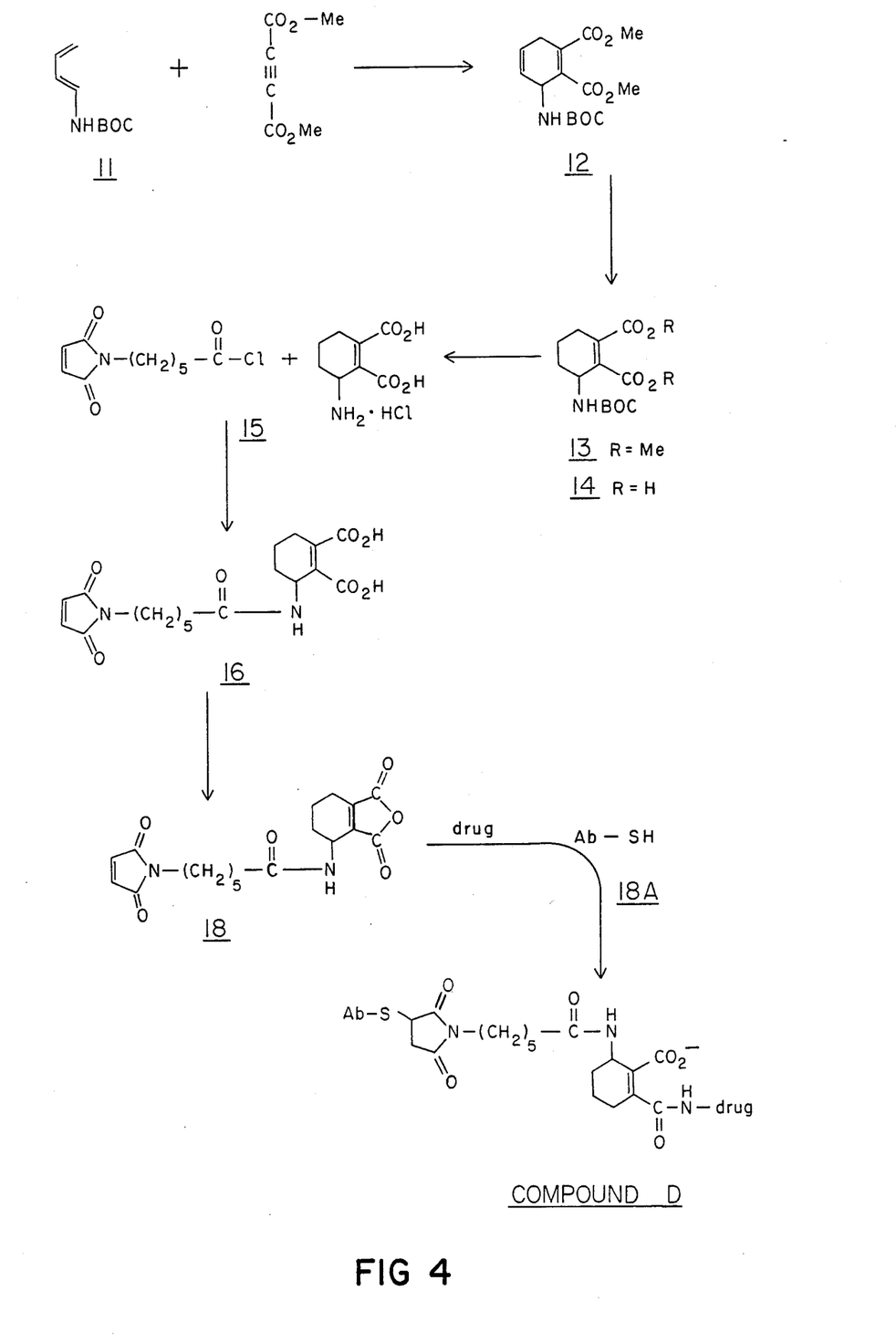

Compound D is synthesized as shown in FIG. 4.

t-Butyl-1,3-butadiene-1-carbamate (11) (10 g, 59.1 mmol) was prepared following the procedure of Overman et al. cite (1978) and was reacted with an equimolar amount of dimethyl acetylenedicarboxylate (8.4 g) in boiling benzene for 4 h. The solvent was then evaporated and the residue purified by flash chromatography on silica gel (petroleum ether - ethyl acetate 80:20 v/v) to give the diester N-t-Butyloxycarbonyl-3-amino-1,4-cyclohexadienyl-1,2-dicarboxylic acid dimethylester 12.

Diene 12(6.7 g, 21.6 mmol) in ethyl acetate (70 mL) was hydrogenated with $H_2$ over a palladium catalyst (10% on carbon, 347 mg) under 1 atm pressure. The reaction was followed by withdrawing samples at different time points for $^1H$ NMR analysis and was judged complete after 1 h. The catalyst was removed by filtration and pure diester N-t-Butyloxycarbonyl-3-amino-1-cyclohexenyl-1,2-dicarboxylic acid dimethylester 13 was obtained after evaporation of the solvent.

Dimethylester 13 (6.6 g, 21.1 mmol) was dissolved in 10% potassium hydroxide in ethanol (65 mL) and the solution was refluxed under $N_2(g)$ for 0.5 h. The cold solution was then poured into cold 1 N hydrochloric acid and the product was extracted with ethyl acetate. The extracts were washed with water, dried, and concentrated, affording a yellowish oil which was further purified by flash chromatography on silica gel with $CHCl_3$-MeOH (9:1 v/v) containing 1% acetic acid as eluant. The pure product N-t-Butyloxycarbonyl-3-amino-1-cyclohexenyl-1,2-dicarboxylic acid 14 was obtained as a foam which solidified upon drying under high vacuum (3.2 g, 12.6 mmol, 58%).

Diacid 14 (135 mg, 0.53 mmol) was kept in 4 N HCl in dioxane (0.5 mL) at room temperature for 20 min. The solution was then concentrated to dryness and the residue was washed with dry ether. Finally, the solid was dissolved in water (10 mL) and the solution was filtered and lyophilized to give pure 3-Amino-1-cyclohexenyl-1,2-dicarboxylic acid hydrochloride salt 15.

Compound 15 can be converted to compound 16 by condensation with 6-maleimidocaproic acid as generally described in the synthesis of compound 5, above.

As with the other diacids, compound 16 can be converted to a heterobifunctional anhydride 18 which is used as a cross-linker to form compound D.

Compound E

Figure 5:
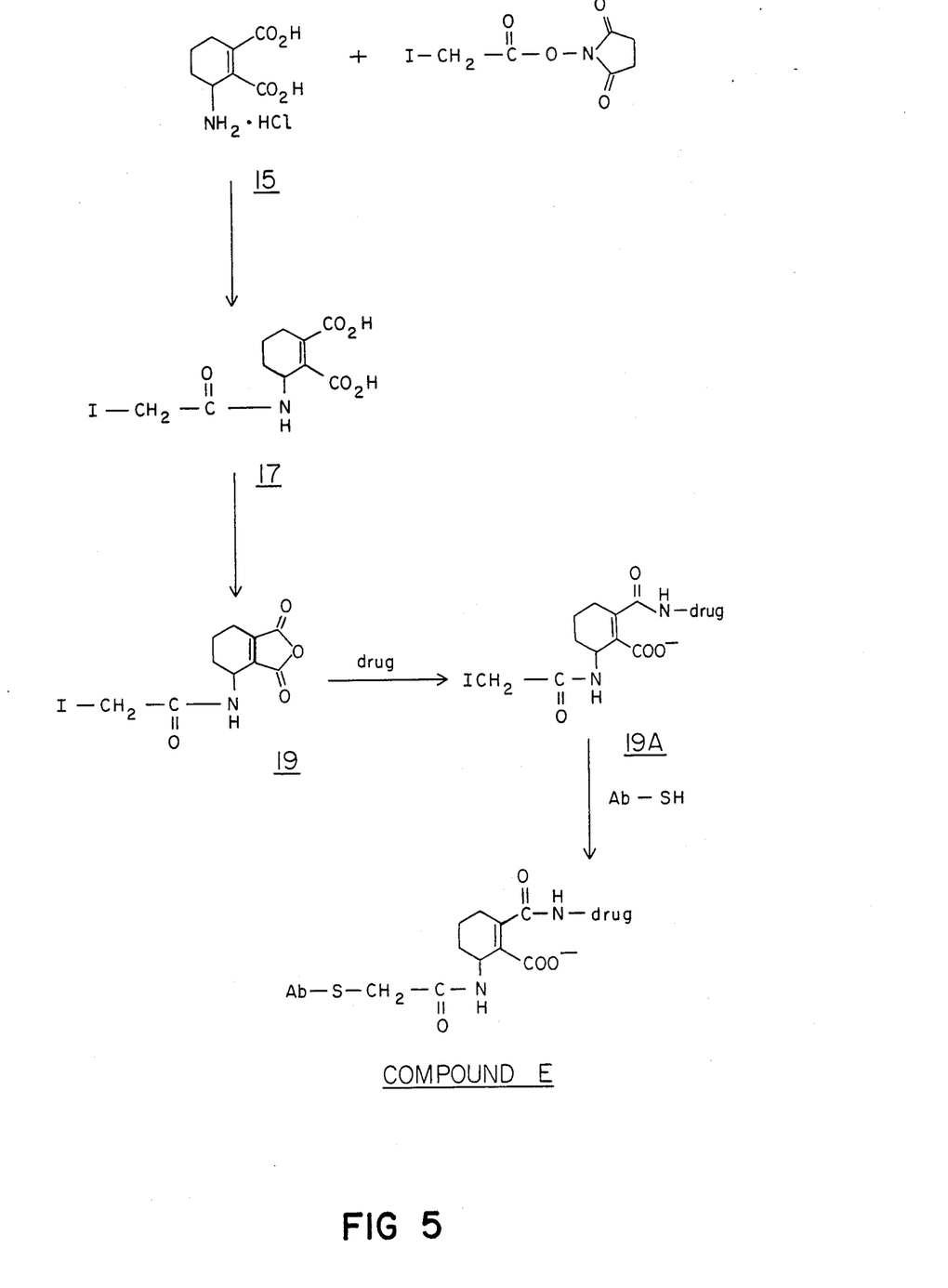

Starting with compound 15, described above, compound E is synthesized as described in FIG. 5 by first forming compound 17, and then forming the anhydride (compound 19). Then the carrier is linked, first with the amino-group-containing substance and then with the antibody, as described below to form compound E.

Compound 17 can be formed in quantitative yield by reacting compound 15 in the usual way with 1 equivalent of the N-hydroxysuccinimide ester of iodoacetic acid in dry dimethylformamide in the presence of a tertiary amine, such as triethylamine or N-ethylmorpholine or alternatively in a mixture of water and dioxane in the presence of an inorganic base, such as sodium or potassium bicarbonate.

Cross-Linking

The cross-linking agents 9, 10, 18, and 19, containing an anhydride function can be used to react with an amino-group-containing drug as described below; the anhydride 4B can be linked to an amino-group-containing drug in the same way. The specific example described utilizes the protein toxin gelonin.

Gelonin is obtained from seeds from *Gelonium multiflorum* (Euphorbiaceae) as described by Stirpe et al. (1980) J. Biol. Chem. 255:6947–6953, who lose a method of preparing gelonin, a protein cytotoxin. The seeds are available from United Chemical and Allied Products, 10 Clive Row, Calcutta-1, India, through the Meer Corporation, North Bergen, New Jersey. A sample of gelonin in sodium phosphate buffer, pH 7.0, is treated at 20° C. for 30 minutes with a 12-fold excess of the anhydride cross-linker in DMSO. The sample is then applied to a column of Sephadex G-25 (superfine) at 4° C. equilibrated with 100 mM sodium phosphate buffer, pH 7.0, containing EDTA (1 mM) to remove excess anhydride cross-linker.

In this way, compounds A, 9A, 10A, 18A, and 19A are formed. For compounds 9A, 10A, 18A, and 19A, a functionalized antibody can then be linked to the compound as described below for a representative antibody, J5, a monoclonal antibody obtained from Coulter Immunology, Hialeah, Florida.

First, the J5 antibody is modified with 2-iminothiolane as described below in order to introduce 2.0 mol sulfhydryl groups per mol antibody.

J5 antibody (2 mg/mL) in 60 mM triethanolamine-HCl buffer, pH 8.0, containing potassium phosphate (7 mM), NaCl (100 mM), EDTA (1 mM), is degassed and then treated with 2-iminothiolane (1 mM) for 90 minutes at 0° C. under nitrogen. Stock solutions of 2-iminothiolane hydrochloride (0.5 M) are prepared as described previously [Lambert et al. (1978) Biochemistry 17:5406–5416]. The reaction is terminated by gel filtration at 4° C. through a column of Sephadex G-25 (fine) equilibrated with 5 mM bistris-acetate buffer, pH 5.8, containing NaCl (50 mM) and EDTA (1 mM). Sulfhydryl groups introduced into the antibody in this way are quantified spectrophotometrically by the method of Ellman (1959) Arch. Biochem. Biophys. 82:70–77.

As described below, the resulting derivatized J5 antibody is mixed with an excess (e.g. 5 molar) of compound 9A, or 18A that has a level of maleimide substitution of 0.7 groups per mol of gelonin. The higher level of substitution of J5 increases the yield with respect to the antibody while the low level of substitution of gelonin reduces the amount of high molecular weight aggregates formed in the cross-linking reaction mixture.

Specifically, modified J5 in buffer (pH 5.8) is mixed with a 5-fold excess of drug-conjugated compound (9A or 18A) in sodium phosphate buffer containing EDTA, and then with triethanolamine-HCl buffer (pH 8.0) to give a final pH of 7.0. After 30 minutes at 0° C., the pH of the solution was raised to 8.5 by adding 1.5 M tris base and the solution concentrated to a small volume (=6 mL) using an immersible ultrafiltration unit (Millipore Corporation, CX-10 filter). The mixture is then applied to a column (95 cm×2.6 cm) of Sephacryl S-300 equilibrated at 4° C. with 100 mM tris-hydrochloride containing 5 mM potassium phosphate, pH 7.5. Gel filtration separates the conjugate and native J5 ($M_r$=160,000) from non-cross-linked gelonin [$M_r$=30,500; Thorpe et al., (1981) Euro. J. Biochem. 116:447–454], and from some high molecular weight aggregates. The major peak, corresponding to a molecular weight range of 160,000 to 220,000 and shown by polyacrylamide/sodium dodecyl sulfate gel electrophoresis to contain both native J5 and cross-linked compounds (e.g. B or D) is pooled and passed through a column (6 mL bed volume) of hydroxylapatite (Bio-Gel HTP) equilibrated in the same buffer. The column is washed with 5 column volumes of buffer and then the bound proteins were eluted with a linear gradient of potassium phosphate from 5 mM to 200 mM in the above buffer. The conjugate eluted from the column free of nonconjugated antibody. The purified conjugate was finally dialyzed against phosphate buffered saline, pH 8.2, for later use and stored.

Similarly, the -SH functionalized antibody can be linked to the iodo compounds 10A and 19A as follows to yield cross-linked compounds C or E. Gelonin was modified with 10 or 19 as described above for 9, 8, 18, but the excess crosslinking reagent was removed with a column of Sephadex G-25 (superfine) equilibrated at pH 8.5 (100 mM triethanolamine-hydrochloride containing 1 mM EDTA). The solutions of the compounds 10A or 19A respectively were then mixed with derivatized J5 containing a sulfhydryl group. Specifically, modified J5 in pH 5.8 buffer was mixed with a 5-fold molar excess of compound 10A or 19A in pH 8.5 buffer and the pH of the mixture was adjusted to 8.5 by adding 1 M triethanolamine base. The reaction mixture was kept at 4° C. for 7 hrs (shorter reaction times also would be sufficient, e.g. 1 hr) and then subjected to the same purification procedure as described above for the J5 conjugate of the compound 9A.

Alternatively Compound A (FIG. 1) is used to synthesize an antibody-drug conjugate by deprotecting the sulfhydryl groups of the polymer, and linking them to an antibody, as follows. Precipitated Compound A, described above, is redissolved in 100 mM triethanolamine-hydrochloride buffer, pH 8.0, and treated with dithioerythritol (3 mg) at room temperature for 0.5 hr to liberate the free sulfhydryl groups for linkage to an antibody bearing a maleimido group. The solution was then passed through a column of Sephadex G-25 (superfine) equilibrated in 100 mM sodium phosphate, pH 7.0, containing 1mM EDTA. The fractions containing the drug carrier A were combined and immediately added to an antibody, which had been modified in the usual way with SMCC (Pierce Chemical Co., Rockford, IL) to introduce a maleimido group (10 mg of J5 antibody). After 30 min at 4° C., the pH of the reaction solution was raised to 8.1 by adding 1.5 M tris base solution. The solution was then concentrated by ultrafiltration to a small volume (5 to 10 mL) and then fractionated on a column (1.6×96 cm) of Sephadex S-300 equilibrated in 10 mM potassium phosphate, pH 8.1, containing 990 mM sodium chloride. Fractions with the antibody-drug carrier conjugate were pooled and the solution diluted with water to achieve a final sodium chloride concentration of 150 mM. This solution was finally concentrated by ultrafiltration to a concentration of about 1 mg of protein per mL. The pH of this solution was checked and if necessary adjusted to 8.1. This final product solution was either stored in the cold or used for biological tests.

Acid Cleavage

The purified compound, e.g. one of the compounds B or D can be administered to a population of cells that includes normal cells and common acute lymphoblastic leukemia cells that exhibit a surface antigen recognized by J5 antibody. The J5 component in the complex will retain its ability to bind selectively to cells with that surface antigen. The gelonin component of the complex will exhibit reduced ability to stop protein synthesis in comparison to native, non-cross-linked gelonin. Gelonin activity can be determined by the rabbit reticulocyte lysate system such as the system available from New England Nuclear Company, Boston MA. However, once the gelonin component of the complex is released by exposure to acidic pH, its ability to inhibit protein formation is indistinguishable from that of native (non-cross linked) gelonin.

Thus, compounds B, C, D, and E have cell-recognition capability, and once the antibody binds to the cell, the complex will be internalized into a cell compartment where cleavage occurs. Specifically, receptors which are internalized by receptor-mediated endocytosis pass through acidified compartments known as endosomes or receptosomes [de Duve (1983) Eur. J. Biochem. 137:391–397]. Thus, the complex will be exposed transiently to an acidic pH sufficient to cleave the active amino-group-containing substance.

Cleavage of native gelonin from compounds B–E will be relatively rapid with good yields below about pH 6.5.

For a given drug-antibody complex, one skilled in the art will recognize that the yields and release rates can be measured for the pH and temperature conditions that are experienced in the release environment, and on that basis the amount of complex necessary to provide sufficient active substance to the target cells can be determined. For example, protein drug release can be determined using polyacrylamide/sodium dodecyl sulfate gel electrophoresis.

A method for testing the release rate of gelonin under varying pH conditions is exemplified by the following procedure.

Samples of compound A are exposed to pH values of 4.0, 5.0, and 6.0, using citric acid-phosphate buffers. The solutions are incubated at 37° C., and samples withdrawn at different times and analyzed for gelonin activity in a cell-free reticulocyte lysate protein synthesis assay, and analyzed also by polyacrylamide/sodium dodecyl sulfate gel electrophoresis.

Compounds 10, 18, and 19 can be used as described by Lambert et al. (1981) J. Mol. Biol. 149:451–476; Wang et al. (1974) Isr. J. Chem. 12:375–389; Lomant et al. (1976) J. Mol. Biol. 104:243–261; Lutter et al. (1974) FEBS Letters 48:288–292; or Coggins et al. (1976) Biochemistry 15:2527–2532 to analyze complex structures containing many polypeptide chains.

A polypeptide chain of interest is functionalized with a sulfhydryl group and exposed to the cross-linking reagent 9, 10, 18, or 19. An amino group of an adjacent chain will form the cleavable amide link at pH 7 or above. Hydrolysis of the amide link at a pH that does not denature the chains (e.g. pH 4 to 5) can be followed, e.g. by polyacrylamide/sodium dodecalsulfate gel electrophoresis to identify the chains adjacent to the chain of interest. The ability to control hydrolysis under non-denaturing conditions, non-oxidative, and non-reducing conditions is particularly important. It is also important to be able to form the cross-link to any amino-containing chain site, and not merely to rely upon the availability of free sulfhydryl groups which are inside the molecule.

Finally, any of compounds A–E can be used to deliver the drug to an aqueous medium by controlling the pH of this medium.

Other Embodiments

Other embodiments are within the following claims. For example, other drug-delivery complexes and protein-evaluation cross-linkers are within the claims.

We claim:

1. A compound having the formula:

where X is an amino-group containing substance whose amino nitrogen forms an amide link with the carbonyl group of the cyclohexene-1, 2,dicarboxylic acid function; $R_1$, $R_2$, and $R_3$ are independently selected from hydrogen, alkyl, or phenyl groups; and F comprises an organic macromolecule function from which the amino-group containing substance is to be released.

2. The compound of claim 1 wherein X comprises a polypeptide residue.

3. The compound of claim 2 wherein the polypeptide is a drug or an enzyme.

4. The compound of claim 1 wherein X is a residue of a cytotoxin.

5. The compound of claim 4 wherein X is a residue of a cytotoxin that inactivates cellular protein synthesis.

6. The compound of claim 4 wherein X is a residue of pokeweed antiviral protein, ricin A-chain, abrin A-chain, modeccin A-chain or gelonin.

7. The compound of claim 1 wherein F comprises a polymeric carrier, an antibody, or a binding partner for a cell-surface receptor.

8. The compound of claim 1 wherein F is and A comprises the organic macromolecule.

9. The compound of claim 8 wherein A is selected from:
(a) polymeric carriers;

(b) N-alkyl maleimido-linked polypeptides; and
(c) thioether-linked polypeptides.

10. The compound of claim 1 wherein $R_1$, $R_2$, and $R_3$ are each —H.

11. The compound of claim 7 wherein F comprises an antibody that is specific for a cell surface receptor of said cell type.

12. The compound of claim 7 wherein F comprises an antibody to a T-cell surface antigen.

13. The compound of claim 12 wherein said T-cell surface antigen is T3, T4, T11, or T12.

14. The compound of claim 7 wherein F comprises an antibody to a tumor associated surface antigen.

15. The compound of claim 7 wherein F comprises J5 antibody.

16. The compound of claim 7 wherein F comprises a binding partner for said cell receptor of cells of a desired cell type, said compound selectively binding to cells of said cell type, being internalized by said cells by cytosis, and being cleaved in acidified organelles of said cells.

17. The compound where:
(a) $R_1$, $R_2$, $R_3$ are independently selected from hydrogen, alkyl, or phenyl groups;
(b) T is selected from —OH, where Z is an N-alkyl maleimido group, I—CH$_2$— or Br—CH$_2$—; and
(c) U and V are independently selected from —OH, and OR$_4$ (R$_4$ being a benzyl group or an alkyl group of C$_5$ or less).

18. The compound of claim 17 wherein $R_1$, $R_2$, and $R_3$ are each —H.

19. A method of using the compound of claim 16 comprising
providing said compound, and
administering said compound to a heterogeneous cell population comprising said cell type and other cells,
said compound selectively binding to and being internalized by said cell type, and being cleaved in an organelle of said cell type responsible for protein synthesis.

20. A method of making the compound of claim 8 comprising the steps:
(a) providing one of the following reagents, (i)

or (ii)

or (iii)

where: X is defined in claim 1, r=1–5, $R_1$, $R_2$, $R_3$ are defined as in claim 8, $R_5$ is —$CH_2I$ or —$CH_2Br$;

(b) reacting said reagent with a functionalized antibody.

* * * * *